Figure 3:
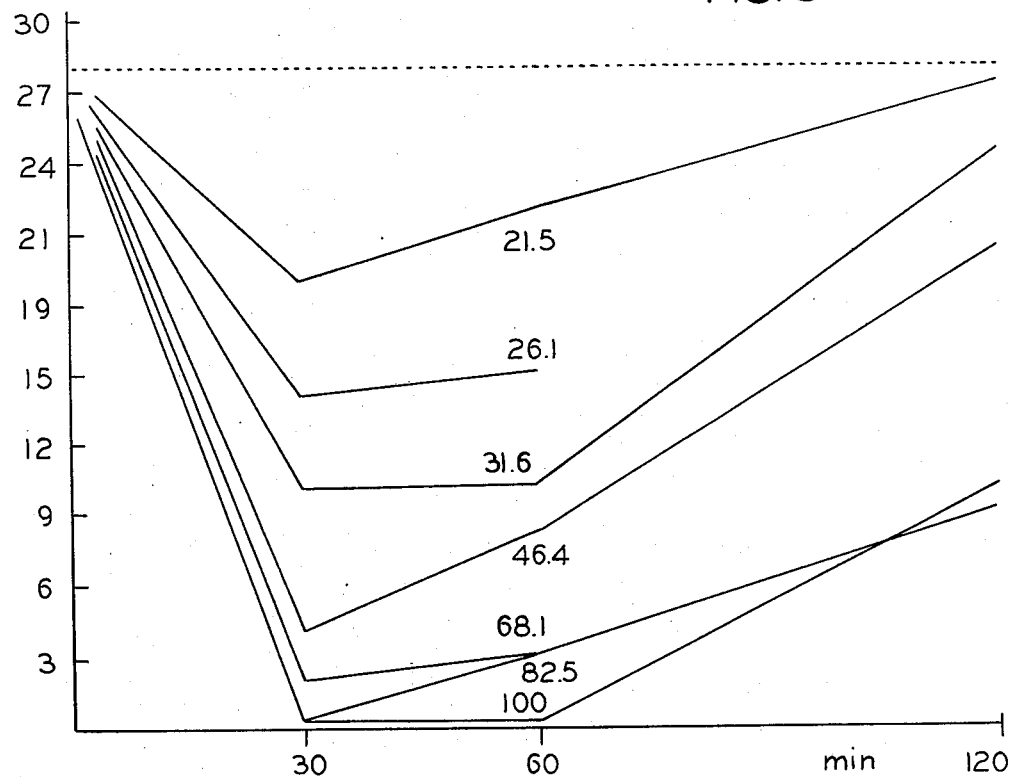

United States Patent [19]
Bolz et al.

[11] 3,992,416
[45] Nov. 16, 1976

[54] 4-OXA-5-HYDROXYPOLYCYCLOALKE-NONES-(3)

[75] Inventors: Gerhard Bolz, Frankenthal;
Walter-Wielant Wiersdorff,
Ludwigshafen, both of Germany

[73] Assignee: BASF Aktiengesellschaft,
Ludwigshafen (Rhine), Germany

[22] Filed: Sept. 9, 1974

[21] Appl. No.: 504,491

[30] Foreign Application Priority Data
Sept. 14, 1973 Germany............ 2346304

[52] U.S. Cl............ 260/343.3 R; 260/343.6
[51] Int. Cl.$^2$............ C07D 307/83
[58] Field of Search............ 260/343.3

[56] References Cited
UNITED STATES PATENTS

| | | |
|---|---|---|
| 2,454,349 | 11/1948 | Schwerdle et al. ............ 260/343.3 |
| 2,454,351 | 11/1948 | Sowa et al. ............ 260/343.3 |
| 2,598,562 | 5/1952 | Kleiman ............ 260/343.3 |

*Primary Examiner*—Anton H. Sutto
*Attorney, Agent, or Firm*—Johnston, Keil, Thompson & Shurtleff

[57] ABSTRACT

New 4-oxa-5-hydroxypolycycloalkenones-(3) and a new method for their production by Diels-Alder reaction of cycloalkapolyenes with 2-hydroxy-2,5-dihydrofuran-5-ones. The new and known compounds obtainable by the process of the invention are starting materials for the production of dyes, plastics, pharmaceutical products and pest control agents.

7 Claims, 4 Drawing Figures

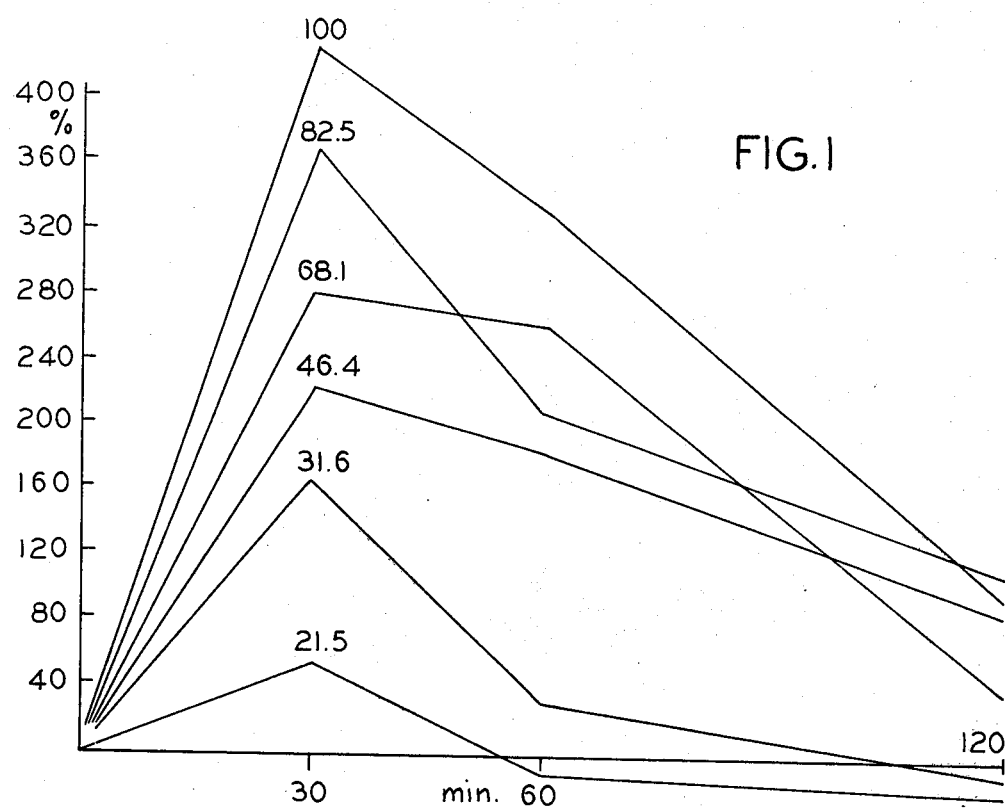
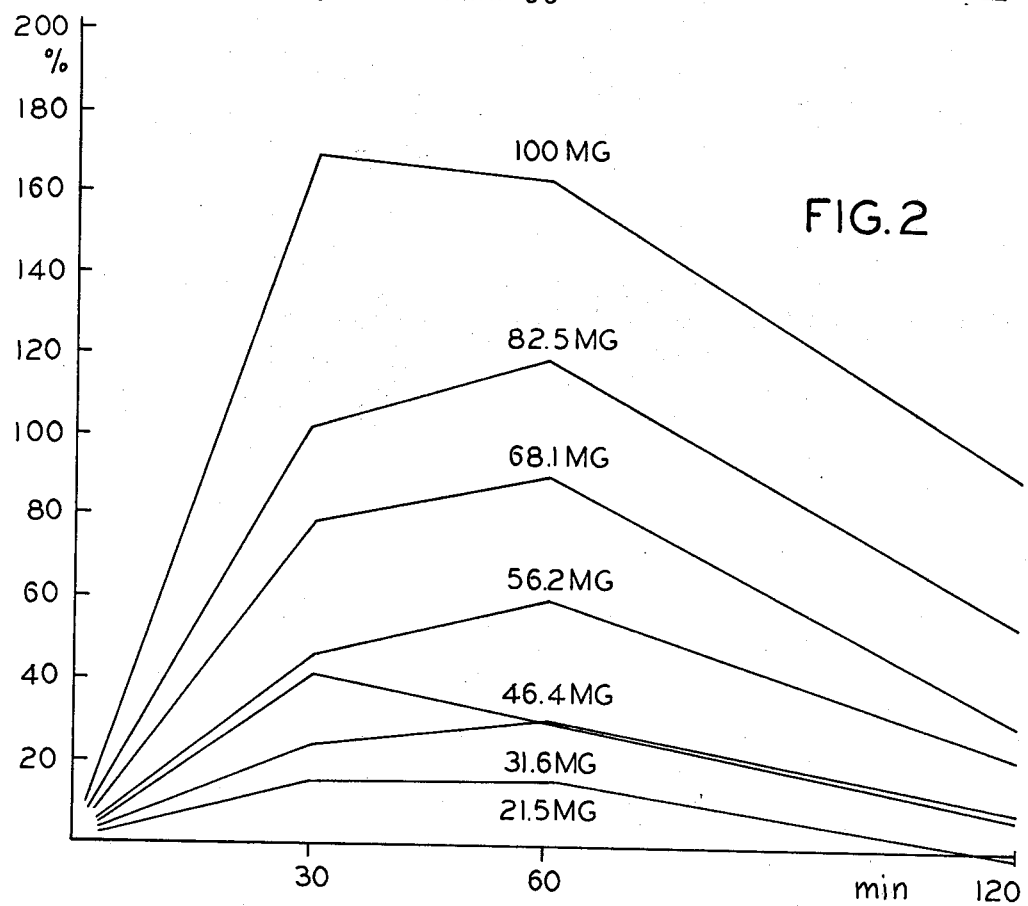

4-OXA-5-HYDROXYPOLYCYCLOALKENONES-(3)

This application discloses and claims subject matter described in German Patent Application No. P 23 46 304.9, filed Sept. 14, 1973, which is incorporated herein by reference.

The invention relates to new 4-oxa-5-hydroxypolycycloalkenones-(3) and a new process for the production of 4-oxa-5-hydroxypolycycloalkenones-(3) by a Diels-Alder reaction of a cycloalkapolyene with a 2-hydroxy-2,5-dihydrofuran-5-one.

It is known from An.Real Soc.Espan.Fis.Quim., volume 54 B, pages 689 to 696 (1958) that butadiene can be reacted in an autoclave at 120° C and a reaction period of eight hours with β-formylacrylic acid in a Diels-Alder reaction; nothing is said about the yields of 2-formyl-4-cyclohexenoic acid thus obtained as the end product. In all other Diels-Alder reactions with other dienes it is not the said acid which is recommended and described as the dienophile but always its pseudo ester, for example the ethyl pseudo ester. It has been found for example that cyclopentadiene can be reacted with the pseudo ester. This result is confirmed in Izv.Akad.-Nauk SSSR, Ser. Khim, No. 8, 1404–1410, 1966 (Bull. Acad. Sc. USSR 1966, pages 1346–1356) which cites the abovementioned Spanish reference; in the case of cyclopentadiene being used as the diene it is always the pseudo ester which is used as dienophile. Entirely in accord with the recommended method 3-formyl-5-norbornene-2-carboxylic acid is only obtained by hydrolysis from the ethyl ester formed as the end product of the Diels-Alder reaction.

The said process is cumbersome, multistaged and quite unsuitable for large scale operation. Isomerization is promoted by the necessary hydrolysis; by-products are formed to an increased extent, even by opening the ring; control and regulation of the reaction are made difficult and unsatisfactory yields of end product are obtained.

One object of this invention is to provide a new process for the simple and economical production of 4-oxa-5-hydroxypolycycloalkenones-(3) in better yields and higher purity.

Another object of this invention is the new 4-oxa-5-hydroxypolycycloalkenones-(3).

We have found that 4-oxa-5-hydroxypolycycloalkenones-(3) of the formula:

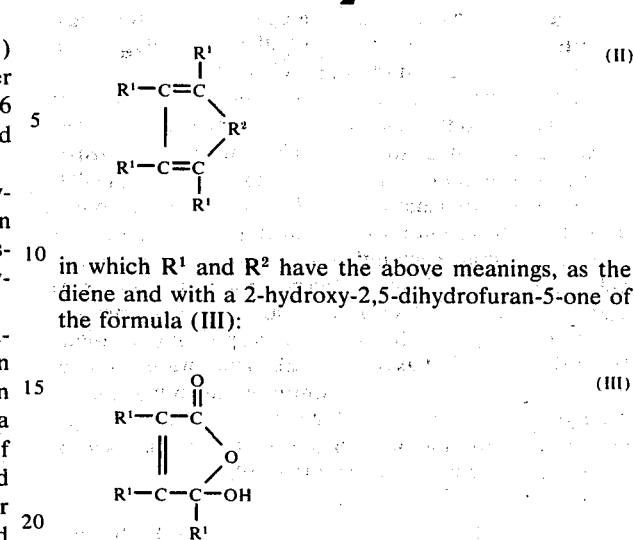

in which the individual radicals $R^1$ may be identical or different and each is hydrogen or an aliphatic radical are obtained advantageously by a Diels-Alder reaction by carrying out the reaction using a cycloalkapolyene of the formula (II):

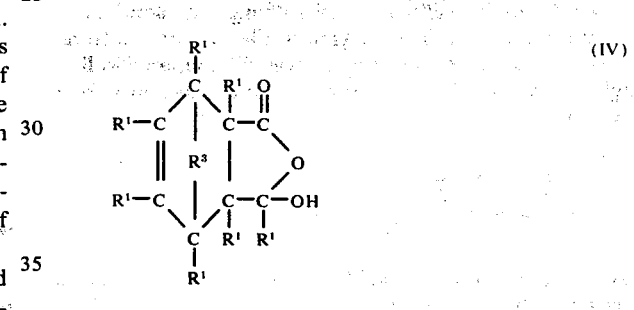

in which $R^1$ and $R^2$ have the above meanings, as the diene and with a 2-hydroxy-2,5-dihydrofuran-5-one of the formula (III):

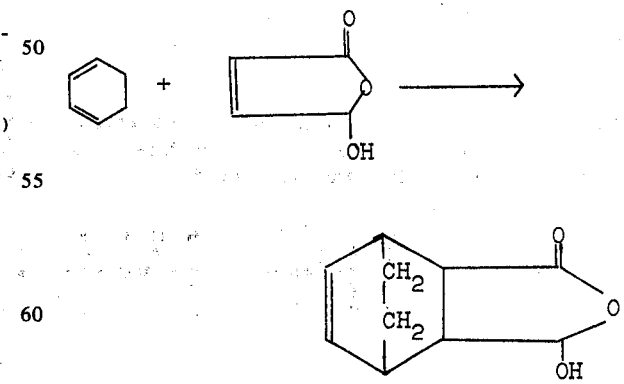

in which $R^1$ has the above meanings, as the dienophile.

We have also found the new 4-oxa-5-hydroxypolycycloalkenones-(3) of the formula (IV):

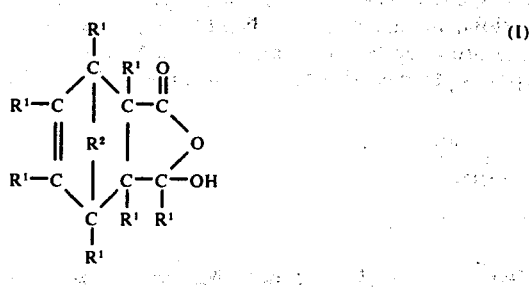

in which the individual radicals $R^1$ are identical or different and each is hydrogen or an aliphatic radical and either $R^3$ is an aliphatic or a cycloaliphatic radical when at least one $R^1$ is an aliphatic radical or $R^3$ (when all the radicals $R^1$ are hydrogen) is a substituted methylene group or an aliphatic radical containing more than one carbon atom or a cycloaliphatic radical.

When cyclohexadiene and 2-hydroxy-2,5-dihydrofuran-5-one are used the reaction may be represented by the following equation:

In comparison with the prior art methods the process according to the invention gives 4-oxa-5-hydroxypolycycloalkenones-(3) in a better yield and higher purity in a simpler and more economical way. It is suitable for large-scale operation and permits in a single stage method a troublefree easily controllable operation under mild conditions. All these advantages are surprising having regard to the prior art.

The reaction is carried out with an excess of one or other starting material or with stoichiometric amounts, conveniently with an amount of from 0.05 to 2 moles of starting material (III) per mole of starting material (II). Preferred starting materials (II) and (III) and consequently preferred end products (I) and (IV) are those in whose formulae the individual radicals $R^1$ are identical or different and each is hydrogen or alkyl of one to eight and particularly of one to four carbon atoms, for example methyl, ethyl, propyl, isopropyl, butyl, isobutyl, amyl or 2-ethylhexyl; $R^2$ is alkylene of one to four and preferably one or two carbon atoms, for example methylene, ethylene, propylene, butylene or isobutylene, alkenylene of two to six and preferably of three to six carbon atoms, particularly the radical

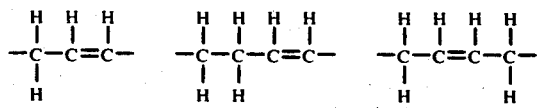

in which the individual radicals $R^4$ may be identical or different and each is hydrogen or alkyl of one to three carbon atoms, for example isopropylidene, an alkadienylene radical of 4 carbon atoms and particularly the radical

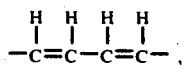

a cycloalkylene radical of three or 4 carbon atoms and particularly the radical

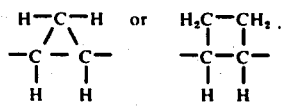

a cycloalkenylene radical of 4 carbon atoms and particularly the radical

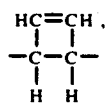

$R^3$ is alkylene of 2 to 4 carbon atoms, substituted methylene, alkenyl or of to six and preferably three to six carbon atoms and particularly the radical

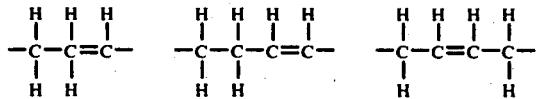

in which the individual radicals $R^4$ may be identical or different and each is hydrogen or alkyl of one to three carbon atoms, for example isopropylidene, an alkadienene radical of 4 to 6 carbon atoms and particularly the radical

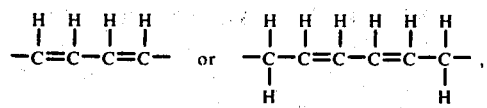

a cycloalkylene of three or four carbon atoms and particularly the radical

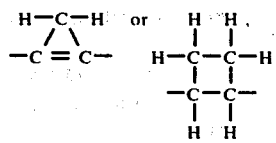

a cycloalkenylene radical of 4 carbon atoms and particularly the radical

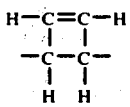

and $R^3$ may also be unsubstituted methylene if at least one radical $R^1$ is an aliphatic radical.

The said radicals may bear, as substituents, groups and/or atoms which are inert under the reaction conditions, for example alkyl groups or alkoxy groups each of one to three carbon atoms, chlorine atoms, or nitro groups. The starting materials may optionally be present in the reaction mixture in tautomeric form, for example cycloheptatriene as norcaradiene-(2,4) of the formula

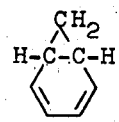

For example the following polyenes are suitable as starting materials (II): cyclopentadiene-1,3, 1-methylcyclopentadiene-1,3, 2-methylcyclopentadiene-1,3, cyclohexadiene-1,3, 2,3-dimethylcyclohexadiene-1,3, 1-isopropylcyclohexadiene-1, cycloheptadiene-1,3, cycloheptatriene-1,3,5, 1-isopropenyl-4-methylcy-

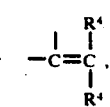

clohexadiene-1,3, dimethylfulvene, α-terpinene, 1,2,3,4-tetramethylcyclopentadiene(1,3), cyclooctatriene-(1,3,5), cyclooctatriene-(1,3,6), cyclooctatetraene, or appropriate mixtures.

The following starting materials (III) are given as suitable examples of dienophiles: 2-hydroxy-2,5-dihydrofuran-5-one, 2-methyl-2-hydroxy-2,5-dihydrofuran- 5-one, 3-methyl-2-hydroxy-2,5-dihydrofuran-5-one, 4-methyl-2-hydroxy-2,5-dihydrofuran-5-one, 2-ethyl-2-hydroxy-2,5-dihydrofuran-5-one, 3-n-propyl-2-hydroxy-2,5-dihydrofuran-5-one, 2-isobutyl-2-hydroxy-2,5-dihydrofuran-5-one, 2,3-dimethyl-2-hydroxy-2,5-dihydrofuran-5-one, 4-ethyl-2-hydroxy-2,5-dihydrofuran-5-one, 2-n-butyl-2-hydroxy-2,5-dihydrofuran-5-one, 2-sec.butyl-2-hydroxy-2,5-hydrofuran-5-one, 2-isobutyl-2-hydroxy-2,5-dihydrofuran-5-one, 2-amyl-2-hydroxy-2,5-dihydrofuran-5-one and 2-hydroxy-2,5-dihydrofuranones bearing two of the said substituents in the 2,3-, 3,4- or 2,4-position.

The reaction is carried out at superatmospheric pressure or preferably at atmospheric pressure, continuously or batchwise, preferably at a temperature of less than 120° C and conveniently from 20° to 110° C and preferably at from 30° to 100° C. It is advantageous to use an organic solvent which is inert under the reaction conditions such as an aromatic hydrocarbon, for example toluene, xylene or benzene; a saturated ketone, for example methyl ethyl ketone, methyl isopropyl ketone, methyl isobutyl ketone or acetone; an ether, for example dibutyl ether, dioxane, tetrahydrofuran, diethyl ether, or ethylene diglycol methyl ether; an alcohol, for example propanol, isopropanol, n-butanol, benzyl alcohol, cyclohexane, cyclohexanol, methanol, ethanol or isobutanol, an aliphatic or cycloaliphatic hydrocarbon such as ligroin, naphtha, cyclohexane, methylcyclohexane, n-hexane, n-pentane and petroleum ether; esters, for example ethyl acetate, methyl formate, ethyl formate and propyl formate; chlorinated hydrocarbons, for example methylene chloride; carbon disulfide; or appropriate mixtures; or mixtures containing water, for example mixtures of an alkanol and water. An amount of up to twenty times the weight of the starting materials (III) is a suitable amount of solvent. One of the starting materials, for example cycloheptatriene-(1,3,5), may be used as solvent for the reaction mixture.

The reaction may be carried out as follows: a mixture of the starting materials (II) and (III), with or without a solvent, is kept at the reaction temperature and advantageously at the said convenient temperature for from 6 minutes to 10 hours. The end product (I) is then isolated from the reaction mixture by a conventional method, for example by distillation of the solvent and recrystallization of the residue, for example from one of the said solvents. The dienophile used as starting material (III) may be used in pure form or in the form of a reaction mixture containing the same for the corresponding syntheses. For example a reaction mixture of hydroxydihydrofuranones which has been synthesized in a conventional way by hydrolysis of an alkoxy derivative may be used. It is also possible to use solutions of the corresponding 2-hydroxy-2,5-dihydrofuranones obtained in the sensitized photooxidation of furan or furan derivatives such as furfurol or methylfuran for example in the presence of a sensitizer such as Rose Bengale; these solutions may be used direct in the process according to the invention or after complete or partial separation of the starting materials (III) for reaction with the diene (II). It is also possible to use for the reaction a solution formed by replacing the original solvent by another, and also a residual solution from which some of the appropriate 2-hydroxy-2,5-dihydrofuran-5-one (III) has been removed, for example mother liquor or uncrystallized residues. An antioxidant such as hydroquinone may if desired be added to the starting mixture.

The new compounds (IV) which can be prepared by the process of the invention and the known compounds (I) are valuable starting materials for the production of dyes, plastics, pharmaceutical materials and pest control agents. Particularly advantageous end products (I) are those from (a) cyclopentadiene, a methylcyclopentadiene and cyclohexadiene and (b) 2-hydroxy-2,5-dihydrofuran-5-one and the appropriate 2-alkyl derivatives (III), particularly 5-methyl4-oxa-5-hydroxytricycloe-[5,2,1,0$^{2,6}$] dec-8-en-3-one, 9-methyl-4-oxatricyclo[5,2,1,0$^{2,6}$]-5-hydroxydec-8-an-3-one, 10-isopropylidene-4-oxa-5-hydroxytricyclo[5,2,1,0$^{2,6}$]dec-8-4-oxa-5-hydroxytricyclo[5,2,2,0$^{2,6}$]undec-8-en-one, and 4-oxa-5-hydroxytetracyclo[5,3,2,0$^{2,6}$0$^{8,10}$]dodec-1-en-3-one. The end products (I) or (IV) may be reacted with isocyanates or carbamyl chlorides by a conventional method to give carbamates which have pharmacological properties, for example for controlling the function of the central nervous system. Reference is made in this context to German Patent Application No. P 23 46 305.0.

The following Examples illustrate the invention. The parts set out therein are parts by weight. They bear the same relation to parts by volume as the kilogram to the liter.

EXAMPLE 1

A solution of 20 parts of 2-hydroxy-2,5-dihydrofuran-5-one and 24 parts of cyclohexadiene-1,3 in 40 parts by volume of tetrahydrofuran is heated in an autoclave for 8 hours at 120° C with an addition of 0.2 part of hydroquinone. The mixture is concentrated. 22.9 parts of 4-oxa-5-hydroxytricyclo[5,2,2,0$^{2,6}$]undec-8-en-3-one (54% of theory) is obtained having a melting point of 151° to 153° C.

EXAMPLE 2

33.2 parts of 2-methyl-2-hydroxy-2,5-dihydrofuran-5-one dissolved in 30 parts by volume of benzene is reacted at 35° C with 23.2 parts of cyclopentadiene in 12 parts by volume of benzene for one hour; after removal of the solvent 50.1 parts (95% of theory) of 5-methyl-4-oxa-5-hydroxytricyclo[5,2,1,0$^{2,6}$]-dec-8-en-3-one is obtained having a melting point of 85° to 87° C after having been recrystallized from a mixture of equal parts of ethyl acetate and n-hexane.

EXAMPLE 3

A solution of 1585 parts of furfurol and 20 parts of Rose Bengale in 5650 parts by volume of methanol is irradiated with a sodium vapor lamp for forty-eight hours while passing oxygen through. The reaction solution contains in addition to unreacted furfurol the reaction products methyl formate and 2-hydroxy-2,5-dihydrofuran-5-one. is 89

300 parts by volume of the reaction solution (58.5 parts of 2-hydroxy-2,5-dihydrofuran-5-one) has 66 parts of cyclopentadiene added to it and then the whole is heated for two hours at 40° C and for half an hour at 60° C. The solvent is removed and the residue is recrystallized from benzene. 86.4 parts of 4-oxa-5-hydroxytricyclo[5,2,1,0$^{2,6}$]-dec-8-en-3-one is obtained having a melting point of 97° to 99° C. The yield is 89% of theory based on 2-hydroxy-2,5-dihydrofuran-5-one.

EXAMPLE 4

A suspension of 250 parts of 2-hydroxy-2,5-dihydrofurane-5-one in 250 parts by volume of benzene is heated to 70° C and reacted in an exothermic reaction at 80° C with a mixture of 100 parts by volume of benzene and 216 parts of methylcyclopentadiene. After one hour the solution is cooled, the solvent is removed and the residue is fractionally recrystallized several times from ethyl acetate. 63 parts (14% of theory) of 9-methyl-4-oxa-5-hydroxytricyclo[5,2,1,0$^{2,6}$]-dec-8-en-3-one is obtained having a melting point of from 129° to 133° C.

EXAMPLE 5

A suspension of 50 parts of 2-hydroxy-2,5-dihydrofuran-5-one in 92 parts of cyclohepta-1,3,5-triene is heated with 0.1 part of hydroquinone for nine hours under reflux. Excess cycloheptatriene is then removed and the residue is filtered through silica gel and concentrated. The residue is recrystallized several times. 15 parts (16% of theory) of 4-oxa-5-hydroxytetracyclo[5,3,2,0$^{2,6}$0$^{8,10}$]dodec-11-en-3-one is obtained having a melting point of 153° to 156° C.

EXAMPLE 6

50 parts of 2-hydroxy-2,5-dihydrofuran-5-one in 500 parts by volume of benzene is heated with 53 parts of dimethylfulvene for 6 hours at 80° C. After the benzene has been removed the residue is crystallized with ethyl acetate and recrystallized several times. 16 parts (16% of theory) of 4-oxa-5-hydrotricyclo[5,2,1,0$^{2,6}$]dec-8-en-3-one is obtained having a melting point of from 116° to 118° C.

The aforementioned carbamates having pharmacological properties, as disclosed in the aforementioned German Patent application, are represented by the general formula (I):

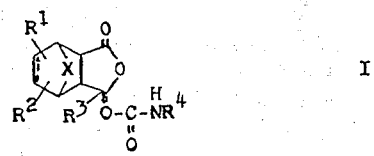

I

In the formula (I) the dotted line represents a double bond which may be hydrogenated;

X is a carbon bridge having a total of from 1 to 10 carbon atoms which may be linear or branched, saturated or unsaturated and may be part of a cycloaliphatic ring;

$R^1$ to $R^4$ may each be hydrogen or a linear or branched alkyl of 1 to 8 carbon atoms;

$R^4$ may also be unsaturated or saturated alkyl or $R^4$ may be a cycloaliphatic, bicycloaliphatic or polycycloaliphatic radical of four to eight ring-carbon atoms or an aromatic radical which may bear substituents.

Examples of the said radicals are: linear or branched saturated carbon bridges for X are for example: methylene, ethylene-1,2, propylene-1,3, propylene-1,2, butylene-1,4, 1,2-dimethylethylene-1,2, 1,1,3-trimethylethylene-1,2 and 1,1-dimethylethylene.

Examples of linear or branched unsaturated carbon bridges for X are: ethylidene-1,2, ethylidene-1,1, 2,2-dimethylethylidene-1,1, 2-ethyl-2-methylethylidene-1,1 and 2,2-diethylethylidene-1,1.

Examples of carbon bridges for X which are part of a saturated or unsaturated cycloaliphatic ring of 3 to 6 members are: cyclopropylene-1,2 cyclobutylene-1,2 and cyclobuten-(3)-ylene-1,2.

Preferred compounds are those in which X is —(CH$_2$)$_n$— where $n$ is an integer of from 1 to 4 and of these ethylene and methylene are particularly preferred.

Examples of radicals for $R^1$ to $R^3$, which may be identical or different, are (in addition to hydrogen): alkyls of up to 8 carbon atoms such as methyl, ethyl, propyl, isopropyl, butyl, isobutyl, sec.-butyl, ter.-butyl, amyl, hexyl, heptyl, 2-ethylhexyl and octyl.

In the preferred compounds $R^1$ to $R^3$ are hydrogen or alkyl of up to 4 carbon atoms.

$R^4$ may have the meanings and preferred meanings given above for $R^1$ to $R^3$. Moreover the alkyls for $R^4$ may be unsaturated. Examples of radicals having double bonds or triple bonds are: vinyl, ally, methallyl, but-1-en-3-yl, but-2-en-3-yl, propargyl, but-1-yn-3-yl, pent-1-yn-3-yl, pent-2-yn-3-yl, 4-methylpent-1-yn-4-yl and 3-ethylpent-1-yn-3-yl.

The alkyls for $R^4$ may bear substituents, for example halogen atoms such as chlorine, bromine or iodine, alkoxy of one to four carbon atoms such as methoxy, ethoxy, propoxy, butoxy or isopropoxy, thioalkyl of one to four carbon atoms such as methylthio, ethylthio, propylthio, isopropylthio or butylthio, dialkylamino of one to four carbon atoms in the alkyl which may bear substituents, or cyclic amino groups of five to seven members in the ring such as dimethylamino, diethylamino, dipropylamino, diisopropylamino, di-n-butylamino, methylethylamino, pyrrolidino, piperidino, morpholino, hexamethylenimino or aromatic radicals and particularly phenyl.

Examples of cycloaliphatic, bicycloaliphatic or polycycloaliphatic radicals for $R^4$ are cyclobutyl, cyclopentyl, 2-methylcyclopentyl, cyclohexyl, cyclooctyl, bicyclo-(2,2,2)-octyl, norbornyl and radicals containing the norbornene or camphor ring system.

Examples of aromatic radicals for $R^4$ are phenyl and phenyl having one or more radicals as substituents, particularly suitable substituents being halogen atoms such as chlorine, bromine or iodine, alkyl and preferably methyl or ethyl, or tert.-amino groups such as dimethylamino or diethylamino.

Examples of substituted phenyl radicals are o-chlorophenyl, m-chlorophenyl, p-chlorophenyl, 3,4-dichlorophenyl, o-toluyl, m-toluyl, p-toluyl, 4-ethylphenyl and 4-dimethylaminophenyl.

In the preferred compounds $R^4$ is hydrogen or linear or branched, saturated or unsaturated alkyl of 1 to 4 carbon atoms which may bear chloro, alkoxy, amino or phenyl as substituents. Examples are methyl, ethyl, propyl, isopropyl, butyl, isobutyl, sec.-butyl, tert.-butyl, vinyl, allyl, β-chloroethyl, methoxymethyl, methoxyethyl, β-ethoxyethyl, propoxymethyl, β-methylthioethyl, β-dimethylamino, β-diethylamino, β-piperidinoethyl, benzyl or β-phenylethyl.

The following compounds are examples of compounds according to the invention:

4-oxa-5-(N-methoxymethylcyrbamoyloxy)-tricyclo[5,2,2,0$^{2,6}$]-undecan-3-one, 4-oxa-5-(N-methylcarbamoyloxy)-tricyclo[5,2,2,0$^{2,6}$]-undecan-3-one, 4-oxa-5-(N-ethylcarbamoyloxy)-tricyclo[5,2,2,0$^{2,6}$]undec-8-en-3-one, 4-oxa-5-(carbamoyloxy)-tricyclo[5,2,2,0$^{2,6}$]undec-8-en-3-one, 4-oxa-5-(carbamoyloxy)-tricyclo[5,2,1,0$^{2,6}$]decan-3-one, 4-oxa-5-(N-n-propylcarbamoyloxy)-tricyclo[5,2,1,0$^{2,6}$]decan-3-one, 4-oxa-5-

(N-β-chloroethylcarbamoyloxy)-tricyclo[5,2,1,0$^{2,6}$]decan-3-one, 4-oxa-5-(N-β-(N',N'-dimethylaminoethyl)-carbamoyloxy)-tricyclo [5,2,1,0$^{2,6}$]dec-8-en-3-one, 4-oxa-5-ethyl-5-(N-methylcarbamoyloxy)-tricyclo[5,2,1,0$^{2,6}$]dec-8-en-3-one, 4-oxa-5-methyl-5-(N-ethylcarbamoyloxy)-tricyclo[5,2,1,0$^{2,6}$]dec-8-en-3-one, 4-oxa-5-(N-methoxymethylcarbamoyloxy)-tetracyclo[5,3,2,0$^{2,6}$0$^{8,10}$]-dodec-11-en-3-one, 4-oxa-5-(N-methylcarbamoyloxy)-tetracyclo[5,4,2,0$^{2,6}$0$^{8,11}$]-trideca-9,12-dien-3-one.

Compounds of formula (I) according to the invention may be prepared by the reaction of a substituted α-hydroylacetone of the general formula (II):

a. with an isocyanate of the general formula (III):

or b. with a carbamoyl chloride of the general formula (IV)

$R^1$ to $R^4$ having the meanings given above.

When an unsaturated compound of formula (II) is used as starting material the double bond may be hydrogenated by a conventional method.

The reaction of compounds of formula (II) with the isocyanates of formula (III) is conveniently carried out in an inert organic solvent, for example tetrahydrofuran, benzene, n-hexane, chloroform or methyl isobutyl ketone at room temperature or an elevated temperature. The presence of a catalyst suitable for the purpose such as dibutyl tin diacetate, tin octanoate or triethylene diamine may be advantageous. The reaction may also be carried out in suspension or in the absence of a solvent.

The reaction of a compound of the formula (II) with a carbamoyl chloride of the formula (IV) may be carried out conveniently in a solvent. It is convenient to add an acid-binding agent, a tertiary organic base, for example pyridine or triehtylamine, an alkali metal carbonate or hydroxide such as potassium hydroxide or an aqueous suspension of calcium oxide. These reactions may also be carried out in a two-phase heterogeneous system.

Hydrogenation of the double bond in the ring system of formula (I) may be carried out without difficulty by a conventional method.

A convenient method consists in dissolving or suspending the appropriate unsaturated carbamate in a solvent which is inert under hydrogenation conditions and hydrogenating it in the presence of a catalyst. Methanol, ethanol, diethyl ether, tetrahydrofuran, dioxane or ayclohexane may be used as solvent. Pd/CaCO$_3$, Pd/carbon, Pt/carbon, platinum dioxide, cobalt or nickel, if desired on a carrier such as SiO$_2$, may be used as catalyst. The hydrogenation may be carried out at room temperature or at elevated temperature and at atmospheric pressure or in an autoclave at superatmospheric pressure depending on the activity of the catalyst. After the necessary amount of hydrogen has been absorbed, the catalyst is removed and the hydrogenation product is purified in the usual way by recrystallization.

The compounds according to the invention have valuable pharmacological properties. They inhibit or stimulate certain functions of the central nervous system. A pronounced antinociceptive effect, for example in the hot plate test, the tail flick test, the writhing test or the Randall-Selitto test may be exhibited in the pharmacological investigation of test animals, the effective dosage being usually far below the range of toxic dosage.

The valuable pharmacological properties of the compounds according to the invention may be shown for example for 4-oxa-5-(N-methylcarbamoyloxy)-tricylo[5,2,1,0$^{2,6}$]dec-8 -en-3-one.

As may be seen from the following graphs, this compound a exhibits a pronounced antinociceptive effect on the test animal, on the mouse in the hot plate test, tail flick test and writhing test and on the rat in the Randall-Selitto test.

1. Hot plate test (FIG. 1)

The hot plate is kept at 57° C and reaction is appraised by the lifting off and simultaneous shaking of the hind legs. The period from being placed on the plate until the occurrence of the said reaction is measured as the latency period. Observation is limited to 30 seconds.

FIG. 1 shows the latency prolongation in percent after different doses (21.5; 31.6; 46.4; 68.1; 82.5 and 100.0 mg/kg of body weight) in dependence on time (in minutes) after application. The percentage latency prolongation is plotted on the ordinates and the time after application (in minutes) on the abscissae.

2. Tail flick test (FIG. 2)

The source of heat used is an incandescent lamp (6 v, 5 w) in a concave reflector. The animals are placed singly in a measuring cage which is at a fixed distance from the heat source and the tail which has been passed out through a slot is irradiated. The period before there is a clear retraction of the tail is measured.

The Figure shows the prolongation of latency in percent after different doses (21.5; 31.6; 46.4; 56.2; 68.1; 82.5 and 100 mg/kg of body weight) in dependence on time after application (in minutes). In FIG. 2 the percentage latency prolongation is plotted as ordinates and the time after application (in minutes) is plotted as abscissae.

3. Writhing test (FIG. 3)

Pain is initiated by p-benzoquinone in a 0.02% aqueous solution in a volume of 10 ml/kg of body weight i.p.. The measurable parameter is the latency (the period up to the first reaction) and the sum of the stretching reactions within fifteen minutes of administration.

FIG. 3 shows the sum of the reactions within 15 minutes after different doses (100.0; 82.5; 68.1; 46.4; 31.6; 26.1 and 21.5 mg/kg of body weight) in dependence on time (in minutes) after application. The sum of the reactions is plotted as ordinates in FIG. 3 and the time after application (in minutes) is plotted as abscissae.

4. Randall-Selitto test (FIG. 4)

The test equipment is the analgesia meter of Ugo Basile (Milan). To increase sensitivity to pain the rat receives 0.05 ml of a 1% aqueous carrageenin solution as a plantar s.c. injection in the left hind paw. The blank measurement is carried out 150 minutes after this injection. After the blank check the test substance is applied and measurement is taken 30, 60 and 120 minutes thereafter.

Figure 4:
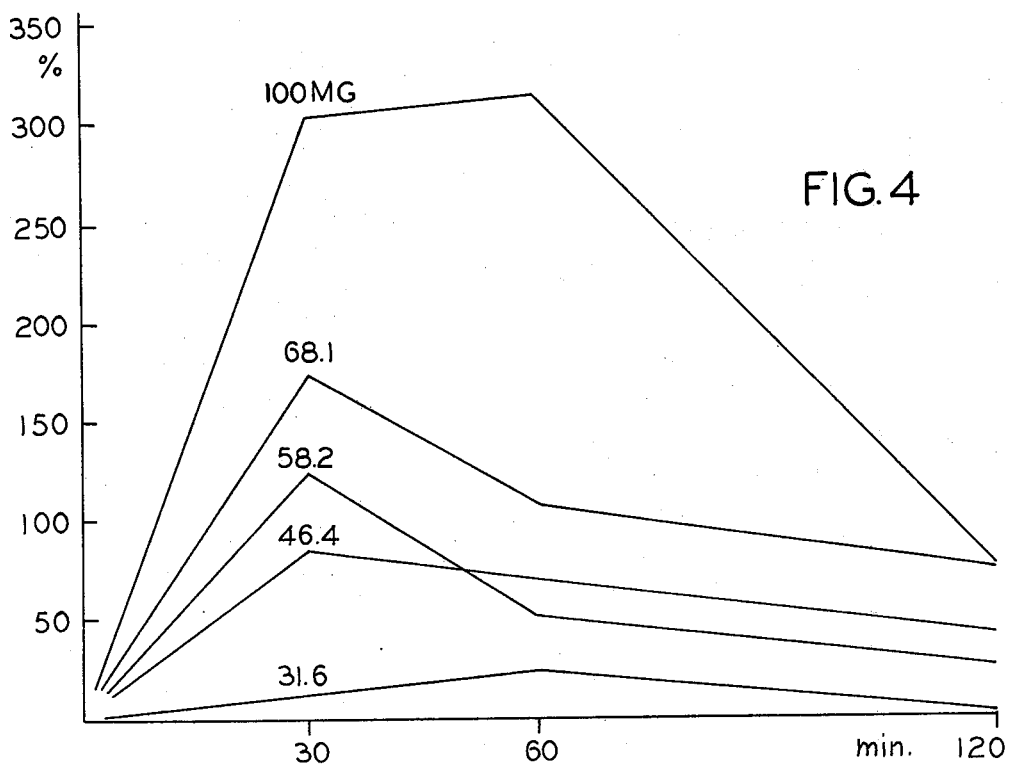

FIG. 4 shows the percentage increase in the paw load endured after different doses (31.6; 46.4; 58.2; 68.1 and 100.0 mg/kg of body weight) in dependence on time (in minutes) after application. The percentage increase in paw load is plotted as ordinates in FIG. 4 and the time after application (in minutes) is plotted as abscissae.

The substance tested has an effect in the analgesia test which is about 10 times as weak as morphine but without impairing respiration and circulation so that in spite of the weaker effect there is a greater therapeutic breadth. The therapeutic breadth is also greater than with dextropropoxyphene with a similar action.

In a pharmacological analysis of the effect on facilitated and unfacilitated reflex discharges of α-motoneurons carried out experimentally the effect mechanism of 4-oxa-5-(N-methylcarbamoyloxy)-tricyclo[5,2,1,0$^{2,6}$]dec-8-en-3-one is about the same as that of morphine and differs clearly from DOLANTIN (Pethidine) and weaker analgesics such as phenacetin, aminophenazone and the like.

In tests on the effect on circulation and respiration in rabbits it is found that there is no appreciable effect on blood pressure and pulse frequency and no change in respiration volume for the said substance up to a dose of 215 mg/kg of body weight, whereas after morphine has been administered in doses of from 3.16 to 21.5 mg/kg of body weight the blood pressure and pulse frequency decline sharply depending on the dose and the respiration volume in this dose range falls to the point of failure of respiration and death of the animal.

Similar pharmacological effects may be shown in the case of other components according to the invention of which the following may be particularly mentioned: 4-oxa-5-(N-methylcarbamoyloxy)-tricyclo[5,2,1,0$^{2,6}$]decan-3-one, 4-oxa-5-(N-methylcarbamoyloxy)-tricyclo[5,2,2,0$^{2,6}$]undec-8-en-3-one and 4-oxa-9-methyl-5-(N-methylcarbamoyloxy)-tricyclo[5,2,1,0$^{2,6}$]dec-8-en-3-one.

While having approximately the same pharmacological effectiveness these compounds have in some cases fewer side effects so that the ratio of effects to side effects is more favorable.

Examples of further effective compounds are as follows: 4-oxa-1-methyl-5-(N-methylcarbamoyloxy)-tricyclo[5,2,1,0$^{2,6}$]dec-8-en-3-one, 4-oxa-5-(N-ethylcarbamoyloxy)-tricyclo[5,2,1,0$^{2,6}$]dec-8-en-3-one, 4-oxa-5-(N-propylcarbamoyloxy)-tricyclo[5,2,1,0$^{2,6}$]-dec-8-en-3-one, 4-oxa-9-methyl-5-(N-ethylcarbamoyloxy)-tricyclo[5,2,1,0$^{2,6}$]dec-8-en-3-one, and 4-oxa-1-methyl-5-(N-methoxymethylcarbamoyloxy)-tricyclo-[5,2,1,0$^{2,6}$]-dec-8-en-3-one.

Therapeutic agents which contain compounds to be used according to the invention may be prepared in a conventional way with suitable carriers or diluents and the conventionally used pharmaceutical auxiliaries in accordance with the desired type of application.

The preferred pharmaceutical preparations are in a form suitable for oral administration. Such forms include tablets, dragees and capsules which can be produced in a conventional manner by the skilled artisan.

We claim:

1. A 4-oxa-5-hydroxypolycycloalkenone-(3) of the formula:

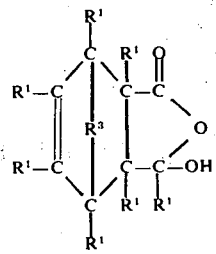

in which the individual radicals R$^1$ are identical or different and each is hydrogen or alkyl of 1-8 carbon atoms, and R$^3$ is alkylene of 2 to 4 carbon atoms, alkenylene of 2 to 6 carbon atoms, an alkadienylene radical of 4 to 6 carbon atoms, a cycloalkylene radical of 3 to 4 carbon atoms, a cycloalkenylene radical of 4 carbon atoms, or one of said divalent radicals or methylene respectively having, as substituents, alkyl of 1-3 carbon atoms, alkoxy of 1-3 carbon atoms, chlorine, or nitro, and R$^3$ may also be unsubstituted methylene if at least one radical R$^1$ is alkyl.

2. A 4-oxa-5-hydroxypolycycloalkenone-(3) as claimed in claim 1 wherein R$^1$ is hydrogen or alkyl of 1-4 carbon atoms, and R$^3$ is alkylene of 2 to 4 carbon atoms; methylene substituted with alkyl or alkoxy each of 1 to 3 carbon atoms, chlorine, or nitro; alkenylene having the formula:

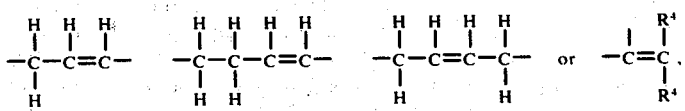

in which the individual radicals R$^4$ may be identical or different and each is hydrogen or alkyl of one to three carbon atoms; an alkadienylene radical having the formula:

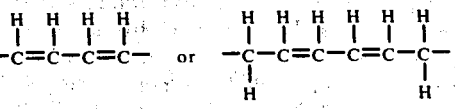

a cycloalkylene radical having the formula:

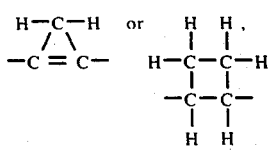
or a cycloalkenylene radical having the formula
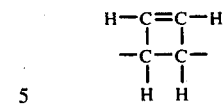
and $R^3$ may also be unsubstituted methylene if at least one radical $R^1$ is alkyl.
3. 5-methyl-4-oxa-5-hydroxytricyclo[5,2,1,0$^{2,6}$]dec-8-en-3-one.
4. 9-methyl-4-oxa-5-hydroxytricyclo[5,2,1,0$^{2,6}$]dec-8-en-3-one.
5. 10-isopropylidene-4-oxa-5-hydroxytricyclo[5,2,1,0$^{2,6}$]dec-8-en-3-one.
6. 4-oxa-5-hydroxy-tricyclo[5,2,2,0$^{2,6}$]undec-8-en-3-one.
7. 4-oxa-5-hydroxytetracyclo[5,3,2,0$^{2,6}$,0$^{8,10}$]dodec-11-en-3-one.
* * * * *